United States Patent
Utterberg (12)

(10) Patent No.: US 6,213,989 B1
(45) Date of Patent: Apr. 10, 2001

(54) HYPODERMIC CANNULA

(75) Inventor: David S. Utterberg, Seattle, WA (US)

(73) Assignee: DSU Medical Corporation, Las Vegas, NV (US)

( * ) Notice: Subject to any disclaimer, the term of this patent is extended or adjusted under 35 U.S.C. 154(b) by 0 days.

(21) Appl. No.: 09/483,522

(22) Filed: Jan. 14, 2000

Related U.S. Application Data

(62) Division of application No. 08/784,599, filed on Jan. 21, 1997, which is a continuation of application No. 08/662,889, filed on Jun. 13, 1996, now abandoned, which is a division of application No. 08/508,545, filed on Jul. 28, 1995, now Pat. No. 5,536,259.

(51) Int. Cl.[7] ....................................................... A61M 5/00
(52) U.S. Cl. ............................................................. 604/272
(58) Field of Search ................................... 604/272, 273, 604/274, 264; 606/222, 223, 224

(56) References Cited

U.S. PATENT DOCUMENTS

| | | |
|---|---|---|
| 2,187,259 | 1/1940 | Barnhart . |
| 2,697,438 | 12/1954 | Hickey . |
| 3,289,675 | 12/1966 | Dunmire et al. . |
| 3,308,822 | 3/1967 | De Luca . |
| 4,368,738 | 1/1983 | Tersteegan et al. . |
| 4,490,139 | 12/1984 | Huizenga et al. . |
| 4,561,445 | 12/1985 | Berke et al. . |
| 4,586,926 | 5/1986 | Osborne . |
| 4,689,040 | 8/1987 | Thompson . |
| 4,826,492 | 5/1989 | Magasi . |
| 5,290,267 | 3/1994 | Zimmermann . |
| 5,405,354 | 4/1995 | Sarrett . |
| 5,484,422 | 1/1996 | Sloane, Jr. et al. . |
| 5,536,259 | * 7/1996 | Utterberg ............................. 604/272 |
| 5,575,780 | 11/1996 | Saito . |

FOREIGN PATENT DOCUMENTS

| | | |
|---|---|---|
| 0 739 639 A1 | 10/1996 | (EP) . |
| 0 739 640 A1 | 10/1996 | (EP) . |
| WO 92/04062 | 3/1992 | (WO) . |

OTHER PUBLICATIONS

Communication from European Patent Office dated Nov. 5, 1997 including Abstract 96304586.9, European Search Report EP 96 30 4586 and Annex to the European Search Report—4 pages total.

* cited by examiner

Primary Examiner—John D. Yasko
(74) Attorney, Agent, or Firm—Garrettson Ellis; Seyfarth Shaw

(57) ABSTRACT

A tissue penetrating cannula comprises a tube having a sharp end formed by a first cut surface defining an acute angle to the longitudinal axis of the tube and forming a generally oval tube edge defining a similar acute angle to the longitudinal axis. A second cut surface is defined along a right hand forward portion of the oval tube edge, and a third cut surface is defined along a left hand forward portion of the oval tube edge. A second and third cut surfaces define between them a forward cutting surface in the tube edge. A fourth cut surface at the point intersects the second and third cut surfaces to cause the cutting surface to be spaced inwardly of the tube outer wall. Fifth and sixth cut surfaces are provided to respectively flatten the tube edge between the first and second surfaces and the first and third surfaces.

5 Claims, 1 Drawing Sheet

HYPODERMIC CANNULA

Cross-Reference to Related Application

This is a division of application Ser. No. 08/784,599, filed Jan. 21, 1997, which is a continuation of application Ser. No. 08/662,889, filed Jun. 13, 1996, abandoned, which, in turn, is a division of application Ser. No. 08/508,545, filed Jul. 28, 1995, now U.S. Pat. No. 5,536,259.

BACKGROUND OF THE INVENTION

Hypodermic cannulas are manufactured by the millions for the many medical uses including blood and solution administration and collection, blood sample taking, and fistula needles for taking and returning blood for processing in a hemodialyzer or the like.

It is known that the best needles from the viewpoint of patient acceptance are the sharpest needles. However, the manufactureability of the needle is also an important factor since commercially successful needles will be manufactured by the millions. Also, such needles must be manufactured with great uniformity from unit to unit, and desirably are highly inexpensive in their manufacturing process.

The expired De Luca U.S. Pat. No. 3,308,822 shows a hypodermic needle having a sharp tip which is formed by five separate cuts of a shaping tool. Such a needle may exhibit certain desirable characteristics of sharpness, but the five separate cuts represent an undue level of complexity in the manufacturing process. Also, the cutting edge extending from the point extends to the outer wall of the cannula.

However, in needles providing vascular access, sharpness can be a problem. In this situation the point of the cannula must rest within the walls of a vessel, but the angle of the point is downward as the needle has been inserted through the skin at an angle. If the cannula is pushed downward, the sharpened point may touch the inside lumen of the vessel. If it pierces the lumen of the vessel a hematoma will result.

Tersteegen et al. U.S. Pat. No. 4,368,738 teaches a bent point cannula to try to avoid this problem. A well-known three bevel sharpened cannula is formed, and then the tip of the cannula is bent upwards much like a ski tip. If the cannula is pushed downward, it is likely that only the underside of the bent-portion will touch the lumen but not damage it.

There are many other problems with this approach. Not only is it very costly to bend a point, but the point can be easily damaged if this operation isn't performed precisely. Also, the bent point requires the cannula be inserted through the skin with the bevel in an abnormal "upside-down" position. Only after the point and bevel is completely within the vessel is the bevel turned "right-side up". In clinical practice, this has shown to be more dangerous than the problem it sought to avoid.

Zimmermann U.S. Pat. No. 5,290,267 and Hickey U.S. Pat. No. 2,697,438 also show similar bent points.

By this invention, a cannula or needle is provided having a simplified manufacturing process, which exhibits extreme incision sharpness for maximized patient comfort, but also protection from hematomas, by means of the point and all forward cutting edges are spaced inwardly from the cannula outer wall.

DESCRIPTION OF THE INVENTION

By this invention, a tissue-penetrating cannula is provided which comprises a tube having a sharp end formed by a first cut surface defining an acute angle, typically about 10° to 30°, to the longitudinal axis of the tube. This first cut surface forms a generally oval tube edge which of course defines a similar acute angle to the longitudinal axis of the tube. The tube is typically made of stainless steel.

A second, cut surface is defined along a right-hand forward portion of the oval tube edge, along with a third, cut surface which is defined along a left-hand forward edge of the oval tube edge. The second and third cut surfaces define between them a forward cutting surface in the tube edge (where a curved surface would have been after the first, flat cut surface was formed, prior to forming the second and third surface).

A fourth, cut surface is provided at the above forwardmost point, the fourth, cut surface intersecting the second and third cut surfaces, causing the forward cutting surface to be radially spaced within the outer wall of said tube. Typically the forward cutting surface is thus formed as substantially a nonlinear point. Without the fourth cut, the forward cutting surface would define a line extending transversely between the inner and outer surfaces of the tube wall.

Preferably, the fourth cut surface is positioned on an outer surface of the tube, being substantially spaced by the wall of the tube from the first, second and third cut surfaces to comprise an outer, undercut bevel.

It is also preferred for the fourth cut surface to define an acute angle of opposite sense to the acute angle of the first cut surface. The planes of the acute angles defined by the first and fourth cut surfaces to the longitudinal axis of the tube are preferably substantially parallel. In other words, if the first and fourth cut surfaces were rotated in the direction of their angles, to become parallel to the longitudinal axis, they would be parallel to each other.

Preferably, the cannula of this invention may be manufactured by cutting a first flat surface at an acute angle to the longitudinal axis tube to form the generally oval tube edge described above. The second cut surface is then formed along the right-hand forward portion of the oval tube edge, while the third, cut surface is formed along the left-hand forward portion of the oval tube edge. This, in turn, forms between the second and third cut surfaces a forwardmost point defining an edge line through the thickness of the wall of the cannula. The second and third cut surfaces are typically in a position that is rotated respectively clockwise and counterclockwise relative to the tube axis by about 10 or 15 to 40 degrees.

Finally, the fourth flat, cut surface is formed at the point or front edge line, intersecting the second and third cut surfaces to reduce the edge line to a substantially non linear point.

Thus, by four machining cuts, a sharp needle point can be formed in accordance with this invention. With computer-directed machining, these cuts may be made in any order.

Alternatively, a six cut embodiment is also shown below.

DESCRIPTION OF THE DRAWINGS

Referring to the drawings.

DESCRIPTION OF SPECIFIC EMBODIMENTS

Figure 1:
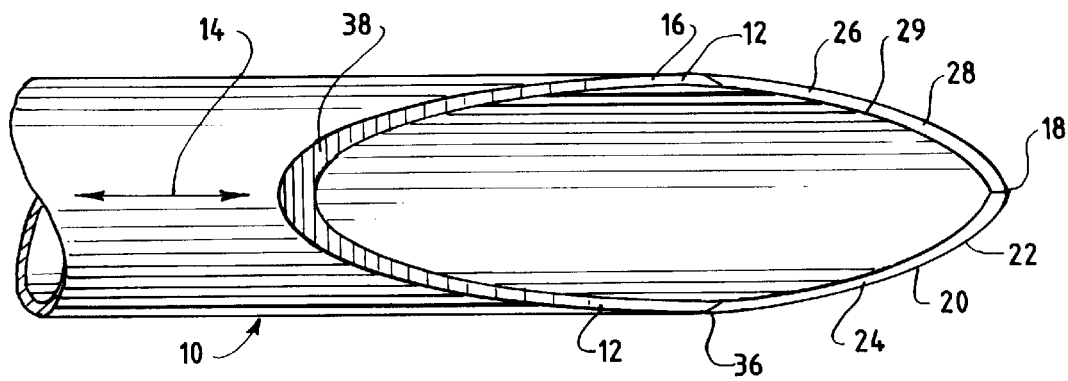
FIG. 1 is an enlarged, plan view of the forward tip of a hypodermic needle in accordance with this invention.

Referring to the drawings, needle 10 may be made of a conventional, stainless steel hypodermic or vascular needle tube of any desired size.

As is conventional, the point on the needle is formed by a first, conventional, flat, cut surface 12, which may be formed by placing the needle 10 in a conventional cutter and making a flat cut 12 defining an acute angle of about 20° with the longitudinal axis 14 of the tubular needle 10. This forms a generally oval tube edge 16.

Figure 2:
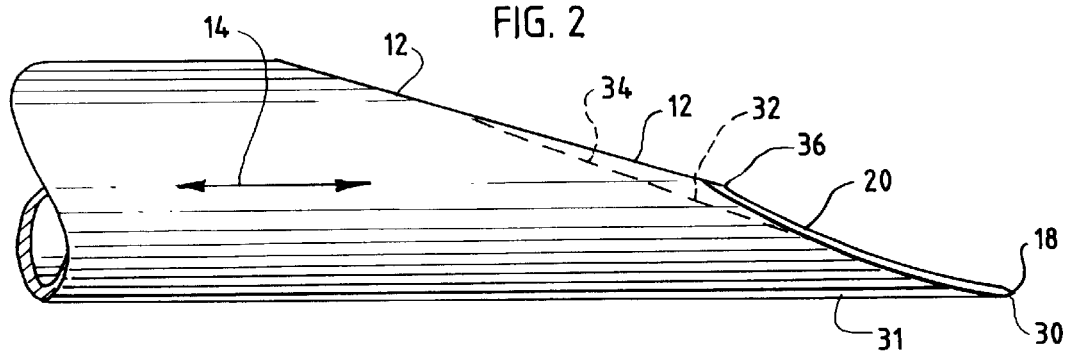
FIG. 2 is a similar enlarged, plan view of the needle of FIG. 1 but rotated 90° about its longitudinal axis.
Figure 3:
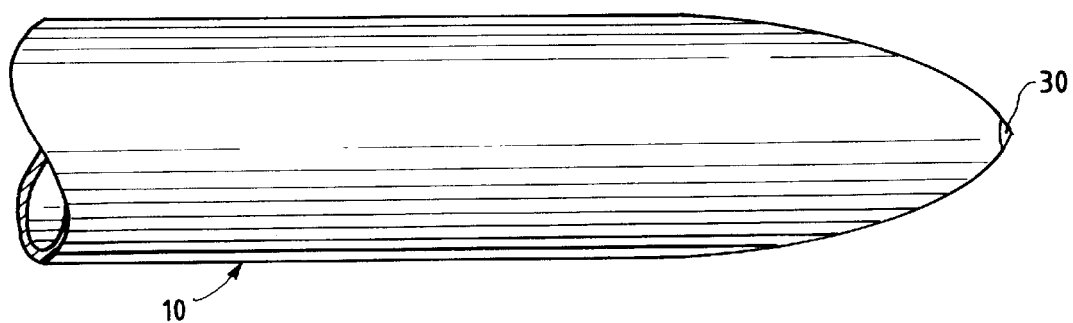
FIG. 3 is an enlarged, plan view of the needle of FIG. 1 but rotated 180° about its longitudinal axis to show the other side of the needle.
Figure 4:
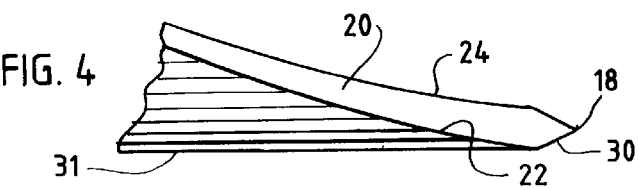
FIG. 4 is an enlarged view of the tip of FIG. 2.

Then, a second cut surface 20 is defined along a right-hand forward portion of the oval tube edge 16 as shown in FIG. 2. This cut may be at a different acute angle to axis 14 from the first cut, with the angle of the cut being slightly canted clockwise at a 14½ degree angle so that the outer edge 22 of second cut 20 is slightly lower than inner edge 24, as shown, provide a tissue cutting edge.

Similarly, a third cut surface 26 is defined along a left-hand forward portion of the oval tube edge 16. In this case also, the cutting angle is twisted in the other direction (counterclockwise) by an equal angle so that the outer edge 28 of cut 26 is slightly lower than the inner edge 30 to provide a tissue cutting edge.

Second and third cuts 20, 26 may be slightly concave.

As the result of this, after the imposition of second and third cuts 20, 26, forward point or cutting surface 18 forms a line extending through the thickness of the tube wall, which, if extended, substantially intersects axis 14, rather like the bow of a ship.

Then, a fourth, typically flat, cut surface preferably defines an acute angle of opposite sense to the acute angle of the first cut surface 12. Also, it is preferred for the planes of the two acute angles to be substantially parallel, i.e., the planes containing axis 14 and perpendicular each of the planes defined by the respective cuts 12, 30. It is preferred for the respective planes thus defined between surface 12 and axis 14 on the one hand, and surface 30 and axis 14 on the other (extending the plane of the surface 30 as necessary to form such an angle), to be parallel.

The intersection of surfaces 20, 26, and 30 forms in the needle tip of this invention a sharpened point 18 which may be substantially non linear at the point of the three intersecting surfaces. Such a point may exhibit essentially the maximum sharpness that can be provided to a needle, imparting to the needle substantial and relatively painless entry through the skin of the patient. At the same time, the needle is relatively easy to manufacture using conventional machine tools, because only four cuts are required to manufacture the needle of this invention, and the sharp point 18 is spaced inwardly from the outer needle wall 31. Alternatively, the sharp point 18 may be a short, linear edge spaced inwardly from outer wall 31, depending on the position of the fourth cut 30.

It can be seen that the area of the fourth flat cut surface is substantially less then the areas of the remaining surfaces, with the fourth surface being substantially spaced by the tube wall from the first, second and third cut surfaces.

FIG. 2 also indicates a optional modification of the needle in accordance with this invention. Fifth and sixth cuts 32, 34 may be respectively made over the first and second cuts 12, 20 and the first and third cuts 12, 26 on opposite sides of the needle tip. By this means, the angled junction 36 between the first and second cuts 12, 20 and the first and third cuts 12, 26 is smoothed out, so that the resulting generally oval tube edge formed by the respective cuts lacks the undesirable peaks 36 on each side of the needle.

It turns out that well known needles have the greatest resistance to insertion forces, not at point 18, but at the beveled transition, where the side bevels 20, 26 coming back from point 18 meet the top bevel 12 coming from the heel 38 of the cut. This beveled transition creates a sharp ridge 36 over which a flap of skin must pass as the needle is inserted. Also, side bevels 20, 26 perform a different function from top bevel 12. The side bevels and the point 18 cut the tissue with inner edges 24, 29 providing cutting action. Top bevel 12 then stretches the incision cut formed by the side bevels. Thus, at point 36, a transition from cutting to stretching is found, which raises needle resistance. The respective fifth and sixth cut surfaces 32, 34 on each side of the needle, when present, can reduce the ridges 36, which, in turn, reduces needle insertion forces.

The above described first through sixth bevels may be ground in traditional manner, or they may be formed by laser cutting equipment, electrical discharge equipment, or the like.

It should also be noted that fifth and sixth surfaces, 32, 34, when present, exhibit a greater angle to axis 14 than first surface 12 and generally a lesser angle to axis 14 than second and third surfaces 20, 26.

Preferably, the length of fifth and sixth bevel surfaces can be as little as 0.1 mm. in length, or as large as 20% of the combined length from the point to the heel of the needle. In other words, the positioning of surfaces 32, 34 in FIG. 2, is substantially enlarged for purposes of clear disclosure. These added surfaces may be canted to provide a cutting edge or may be flat with respect to first cut surface 12 to serve a stretching function for the tissue.

The above has been offered for illustrative purposes only, and is not intended to limit the scope of the invention of this application, which is as defined in the claims below.

That which is claimed:

1. A tissue-penetrating cannula which comprises a tube having an outer wall, and a sharp end defined by a first cut surface defining an acute angle to the longitudinal axis of said tube and forming a generally oval tube edge defining a similar acute angle to said longitudinal axis;

a second cut surface defined along a right hand forward portion of said oval tube edge; a third cut surface defined along a left hand forward portion of said oval tube edge, said second and third cut surfaces defining between them a forward cutting surface in said tube edge; a fifth cut surface extending along said tube edge between said first and second surfaces in a position to flatten said tube edge, compared with a tube edge comprising joined first and second surfaces without said fifth cut surface, and a sixth cut surface extending along said tube edge between said first and third surfaces on a side of said needle opposed to said fifth cut surface in a position to flatten said tube edge, compared with the tube edge comprising joined first and third surfaces without said sixth cut surface.

2. The cannula of claim 1 in which said acute angle is 10° to 30°.

3. The method of forming a point on the end of a tissue-penetrating cannula having an outer wall, which comprises cutting a first surface adjacent to the end of said cannula defining an acute angle to the longitudinal axis of said cannula to form a generally oval tube edge defining a similar acute angle to said longitudinal axis; cutting a second cut surface along a right hand forward portion of the oval tube edge, rotated at a clockwise angle to said first cut surface; cutting a third cut surface along a left hand forward portion of the oval tube edge, rotated at a counterclockwise angle to said first cut surface, whereby said second and third cut surfaces define between them a forwardmost cutting surface in the tube edge; cutting a fifth cut surface along said tube edge between said first and second surfaces in a position to flatten said tube edge, compared with a tube edge comprising joined first and second surfaces without a fifth cut surface; and cutting a sixth cut surface along said tube edge between said first and third surfaces at a position to flatten a portion of tube edge opposed to said fifth cut surface, compared with the tube edge comprising joined first and third surfaces without said sixth cut surface.

4. The method of claim 3 in which said acute angle is 10 degrees to 30 degrees.

5. The method of claim 3 in which said fifth and sixth cutting surfaces are cut respectively after cutting said second and third cut surfaces.

* * * * *